(12) United States Patent
Klenner et al.

(10) Patent No.: US 9,974,921 B2
(45) Date of Patent: May 22, 2018

(54) USABILITY FEATURES FOR RESPIRATORY HUMIDIFICATION SYSTEM

(71) Applicant: Fisher & Paykel Healthcare Limited, Auckland (NZ)

(72) Inventors: Jason Allan Klenner, Auckland (NZ); Andrew Paul Maxwell Salmon, Auckland (NZ); Mark Samuel Hamilton, Auckland (NZ); James William Stanton, Auckland (NZ); Michael John Andresen, Auckland (NZ); Jonathan Andrew George Lambert, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 645 days.

(21) Appl. No.: 14/396,711

(22) PCT Filed: Apr. 26, 2013

(86) PCT No.: PCT/NZ2013/000075
§ 371 (c)(1),
(2) Date: Jan. 13, 2015

(87) PCT Pub. No.: WO2013/162386
PCT Pub. Date: Oct. 31, 2013

(65) Prior Publication Data
US 2015/0096560 A1 Apr. 9, 2015

Related U.S. Application Data

(60) Provisional application No. 61/639,632, filed on Apr. 27, 2012, provisional application No. 61/785,733, filed on Mar. 14, 2013.

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0003* (2014.02); *A61M 16/024* (2017.08);
(Continued)

(58) Field of Classification Search
CPC .. A61M 16/109; A61M 16/16–16/168; A61M 11/041–11/042; F24F 2006/008
See application file for complete search history.

(56) References Cited

U.S. PATENT DOCUMENTS

| 5,303,701 A | 4/1994 | Heins et al. |
| 5,881,393 A | 3/1999 | Marchello |

(Continued)

FOREIGN PATENT DOCUMENTS

| AU | 2000071791 | 3/2001 |
| WO | WO2006/017350 | 2/2006 |
| WO | WO2012/154883 | 11/2012 |

OTHER PUBLICATIONS

Jun. 24, 2013 International Search Report of Application No. PCT/NZ2013/000075 filed Apr. 26, 2013.
(Continued)

*Primary Examiner* — Valerie L Woodward
(74) *Attorney, Agent, or Firm* — Knobbe Martens Olson & Bear LLP

(57) ABSTRACT

A humidification system for delivering humidified gases to a user can include a heater base, humidification chamber having an inlet, outlet, and associated fluid conduit, and breathing circuit including a supply conduit, inspiratory conduit, and optional expiratory conduit. The humidification system can include various features to help make set-up less difficult and time-consuming. For example, the supply conduit, inspiratory conduit, and optional expiratory conduit can be coupled into a one-piece circuit to aid set-up. Various components can be color-coded and can have corresponding
(Continued)

structures to indicate which components should be connected to one another during set-up. Such features can also help make the set-up process more intuitive for an operator, which can reduce the need for specialized training and reduce the number of potential errors.

12 Claims, 23 Drawing Sheets

(51) Int. Cl.
    *A61M 16/00*     (2006.01)
    *A61M 16/08*     (2006.01)

(52) U.S. Cl.
    CPC .... *A61M 16/0816* (2013.01); *A61M 16/0883* (2014.02); *A61M 16/109* (2014.02); *A61M 16/168* (2014.02); *A61M 16/0875* (2013.01); *A61M 2016/003* (2013.01); *A61M 2205/3334* (2013.01); *A61M 2205/3368* (2013.01); *A61M 2205/3372* (2013.01); *A61M 2205/502* (2013.01); *A61M 2205/505* (2013.01); *A61M 2209/06* (2013.01)

(56) References Cited

U.S. PATENT DOCUMENTS

| | | | |
|---|---|---|---|
| 6,435,180 B1 * | 8/2002 | Hewson | A61M 16/16 128/203.12 |
| 6,631,718 B1 | 10/2003 | Lovell | |
| 7,743,767 B2 | 6/2010 | Ging et al. | |
| 7,874,291 B2 | 1/2011 | Ging et al. | |
| 8,245,709 B2 * | 8/2012 | Rossen | A61M 16/16 128/200.24 |
| 8,783,252 B2 | 7/2014 | Pierro et al. | |
| 2003/0066526 A1 | 4/2003 | Thudor et al. | |
| 2004/0055597 A1 * | 3/2004 | Virr | A61M 16/16 128/203.12 |
| 2007/0169776 A1 * | 7/2007 | Kepler | A61M 16/0051 128/200.23 |
| 2009/0044808 A1 | 2/2009 | Guney et al. | |
| 2009/0056712 A1 * | 3/2009 | Cortez, Jr. | A61M 16/08 128/203.26 |
| 2011/0017212 A1 * | 1/2011 | Kenyon | A61M 16/00 128/203.26 |
| 2012/0073573 A1 * | 3/2012 | Thudor | A61M 16/16 128/203.26 |
| 2014/0090649 A1 | 4/2014 | Groll et al. | |
| 2014/0202463 A1 | 7/2014 | Ging et al. | |

OTHER PUBLICATIONS

Sawyer, Dick, et al. "An introduction to human factors in medical devices." *US Department of Health and Human Services, Public Health Service, Food and Drug Administration, Center for Devices and Radiological Health* (1996).

* cited by examiner

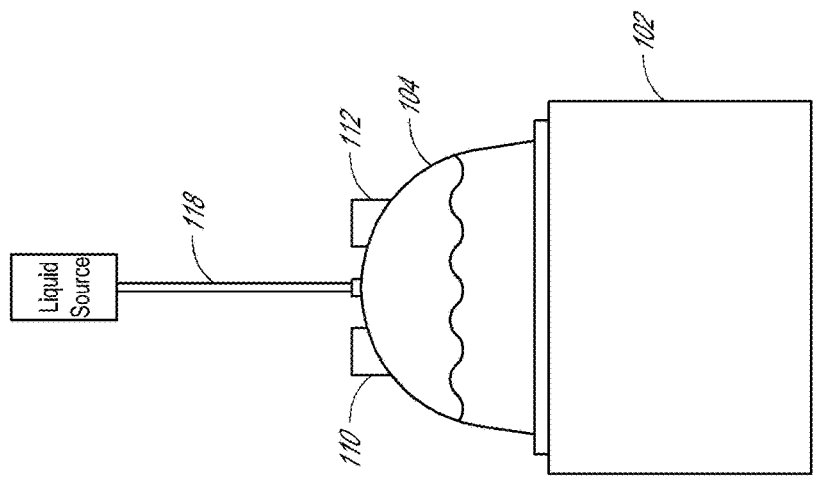

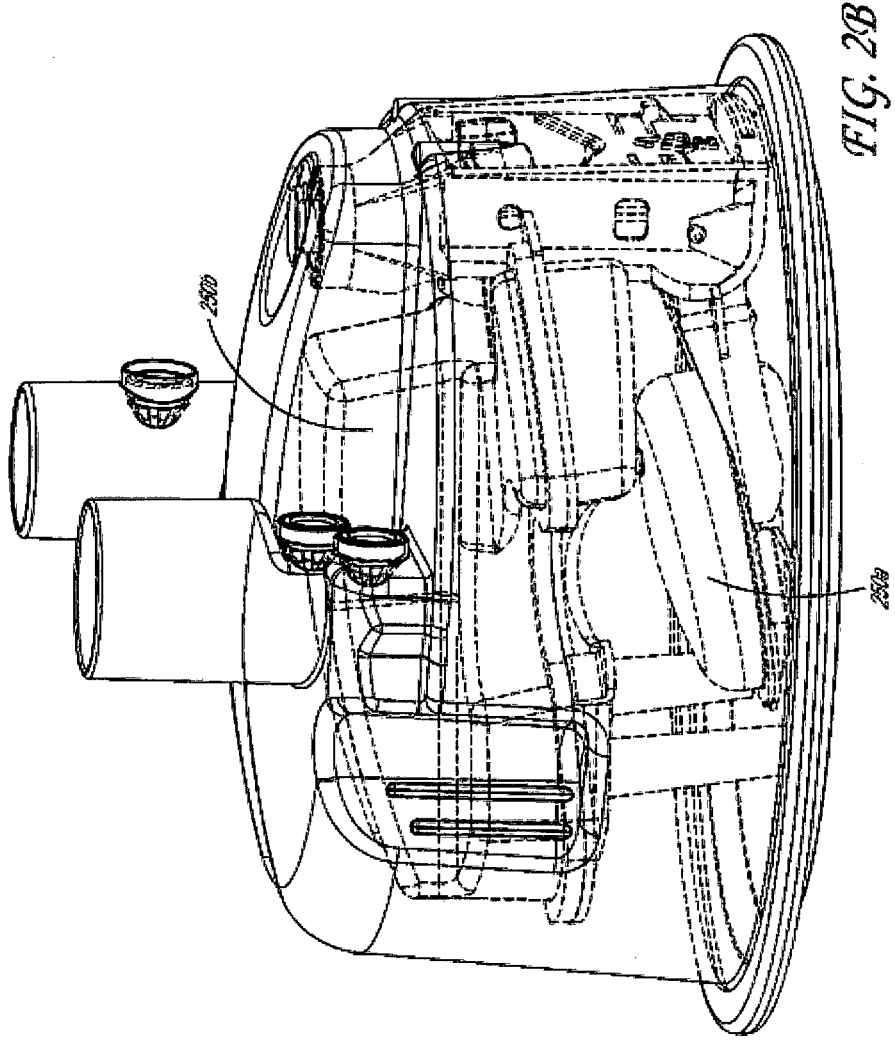

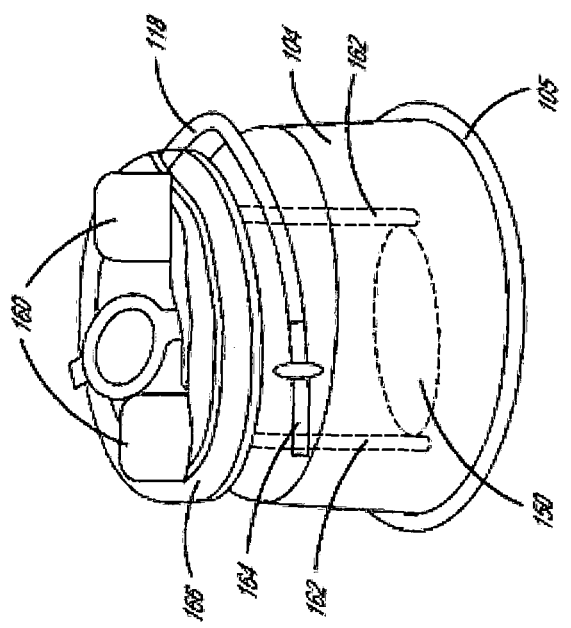
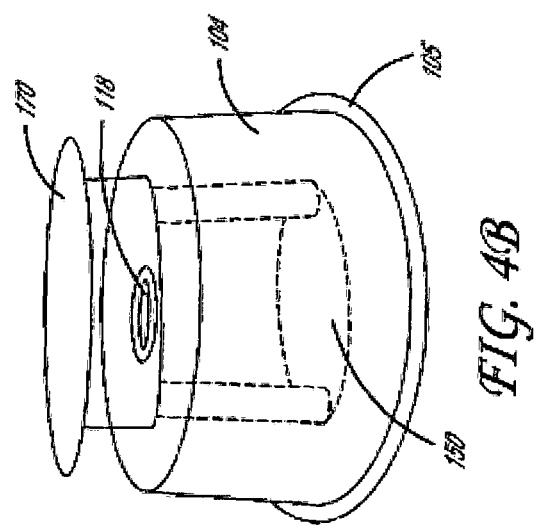

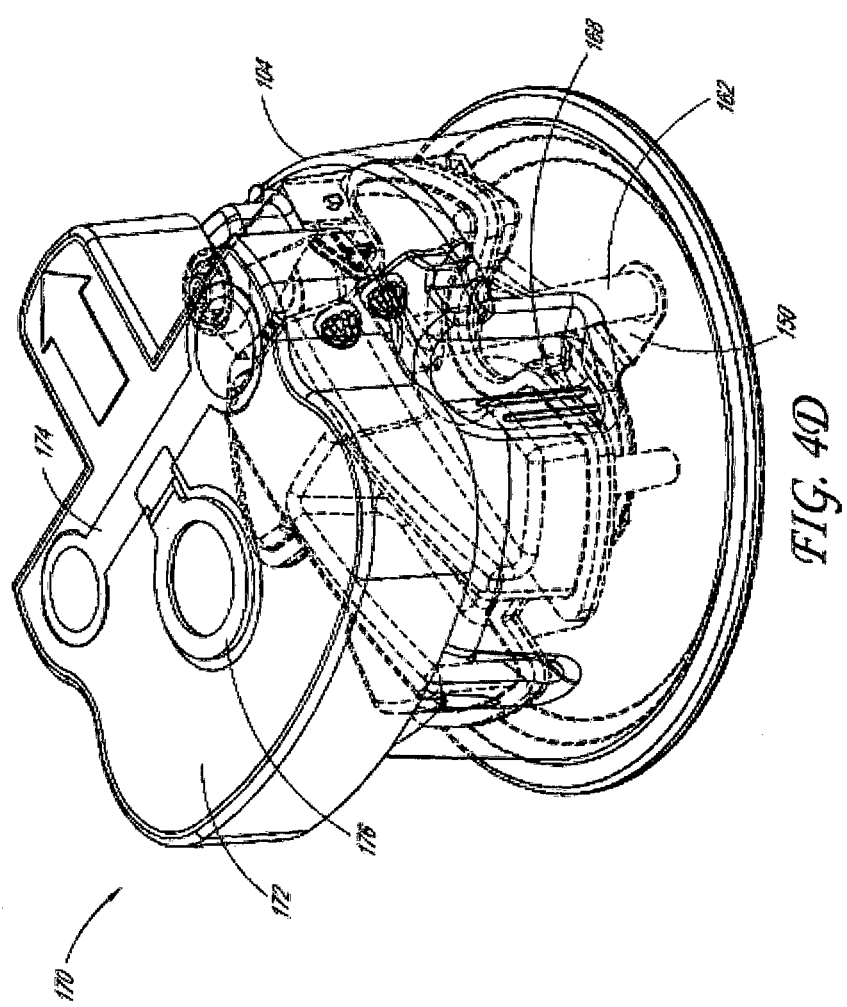

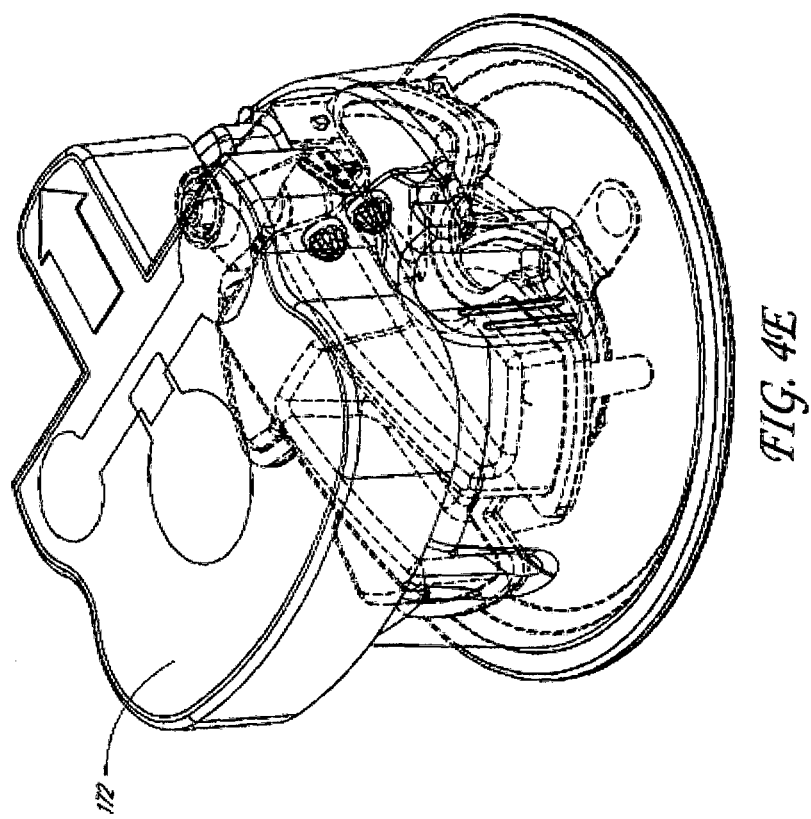

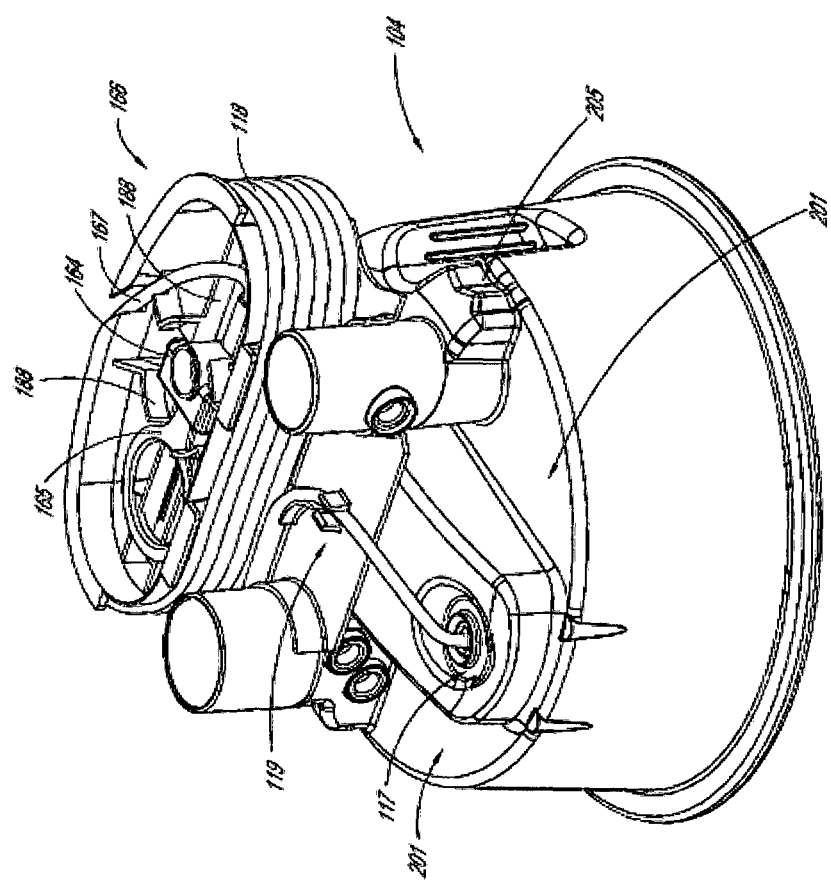

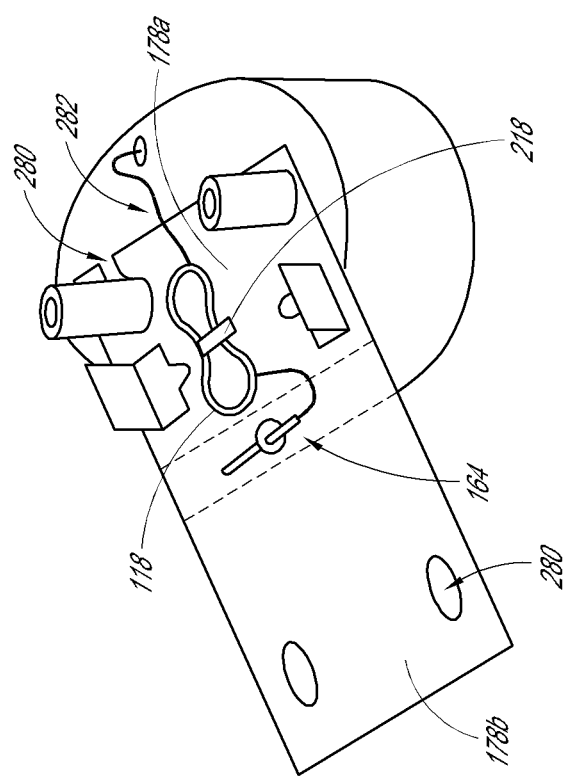
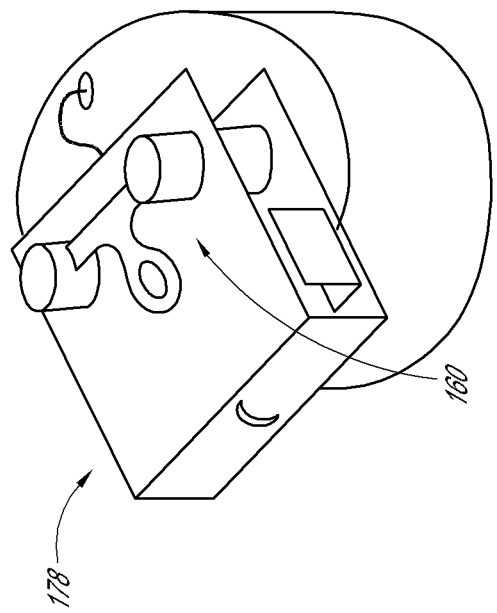
FIG. 4G1
FIG. 4G2

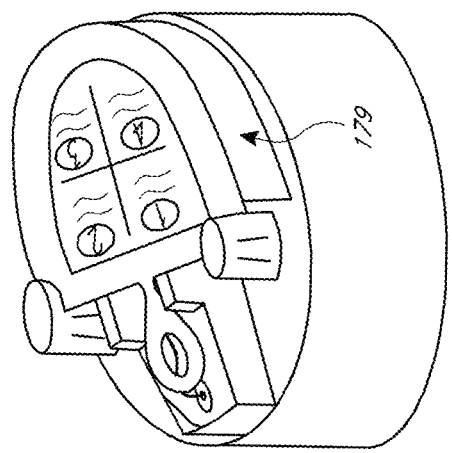
FIG. 4H2
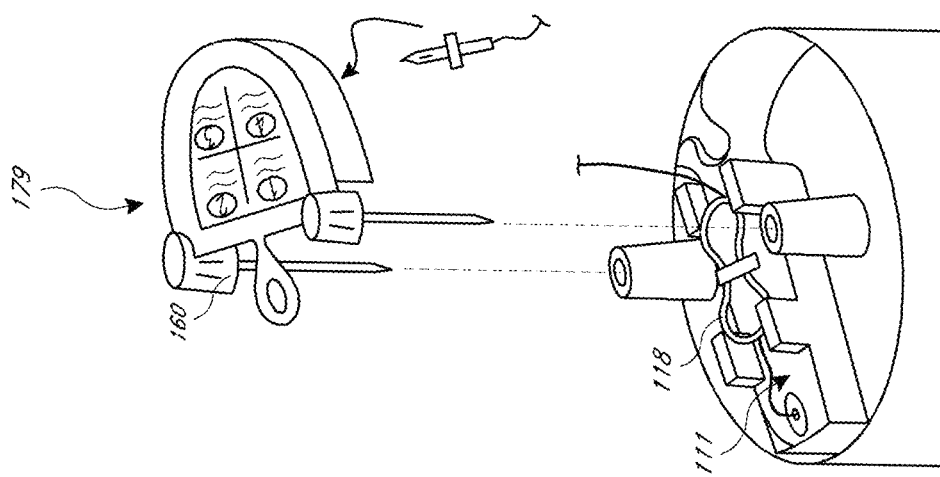
FIG. 4H1

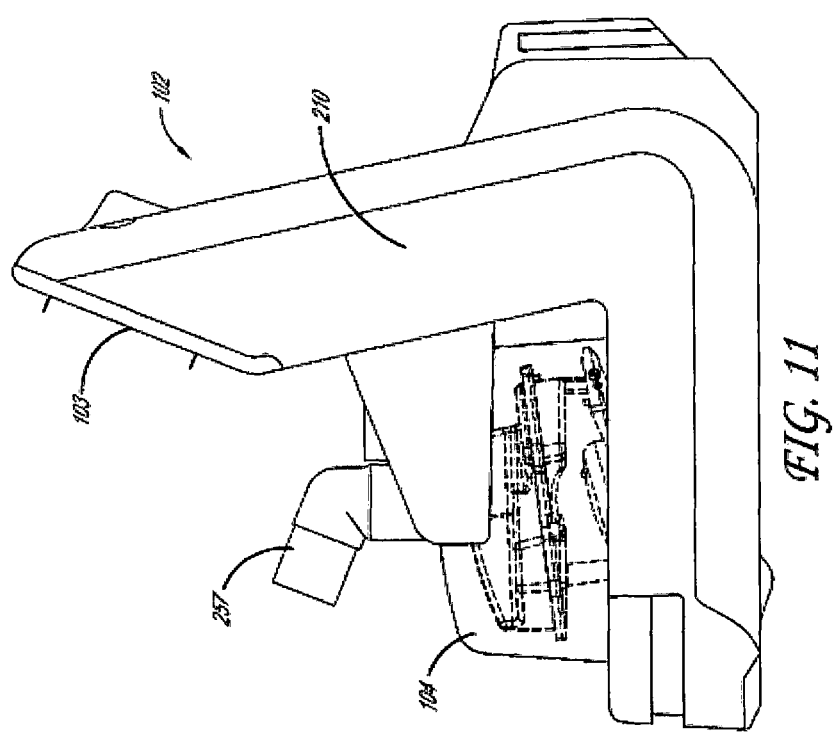

USABILITY FEATURES FOR RESPIRATORY HUMIDIFICATION SYSTEM

CROSS-REFERENCE TO RELATED APPLICATIONS

The present application claims the priority benefit of U.S. Provisional Application Nos. 61/639,632, filed Apr. 27, 2012, and 61/785,733, filed Mar. 14, 2013, the entirety of each of which is hereby incorporated by reference herein.

BACKGROUND

Field of the Invention

The present disclosure generally relates to humidification systems for humidifying gases supplied to users, and more particularly, to humidification systems having features for improved assembly and usability.

Description of the Related Art

Many gas humidification systems deliver heated and humidified gases for various medical procedures, including respiratory treatment, laparoscopy, and the like. These systems can be configured to control temperature, humidity and flow rates through the use of various sensors.

Various components of such systems also can include features designed to help control the system and/or help provide users with gases having desired characteristics. Such gas humidification systems can include many components that must be assembled prior to use. The set-up process can be complicated and time-consuming, and may require specialized training. The specialized training may need to be repeated for each new employee or user. Thus, there is a need for a system that is intuitive to assemble and use without extensive training.

SUMMARY

A humidification system for delivering humidified gases to a user can include a heater base, a humidification chamber having an inlet, outlet, and associated liquid conduit, and a breathing circuit including a supply conduit, inspiratory conduit, and optional expiratory conduit. A humidification system can include various features as described herein to help make set-up less difficult and time-consuming. Such features can also help make the set-up process more intuitive for an operator, which can reduce the need for specialized training and reduce the number of potential errors.

In some embodiments, the humidification chamber is packaged with the inlet and outlet ports covered by a port cap. The port cap is designed to help indicate to the operator that the port cap should be removed and discarded during set-up. In some embodiments, the liquid conduit, or feedset, is contained and concealed by the port cap so that the feedset cannot be connected to a liquid source until the port cap is removed.

In some embodiments the supply conduit, inspiratory conduit, and optional expiratory conduit are coupled into a one-piece assembly to aid set-up. The conduits can be coupled by, for example, a mesh sheath, clips, or any other appropriate coupling mechanism. One or more of the conduits can be removably coupled to the others. The expiratory conduit can include an electrical plug configured to be connected to a socket on the heater base to power a heating element within the conduit. In some embodiments, one or more of the conduits can include integrated sensors and adaptor cables to connect the sensors to the heater base.

In some embodiments, various components of a humidification system are color-coded and can have corresponding structures to indicate which components should be connected to one another during set-up. The heater base and/or consumables packaging can also include a schematic or step-by-step instructions to help guide the operator through the set-up procedure.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects and advantages of the present disclosure will be described with reference to the following drawings, which are illustrative but should not be limiting of the present disclosure.

FIG. 2A illustrates an example embodiment of a humidification chamber installed on a heater base;

FIG. 2B illustrates an example embodiment of a humidification chamber;

FIGS. 4A-4H2 illustrate example embodiments of a humidification chamber as packaged;

FIGS. 8A-9C illustrate example embodiments of conduits having features corresponding to those shown in FIG. 7B;

FIG. 11 illustrates an example embodiment of a heater base and humidification chamber.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the present disclosure should not be limited by any particular embodiments described below.

Figure 1:
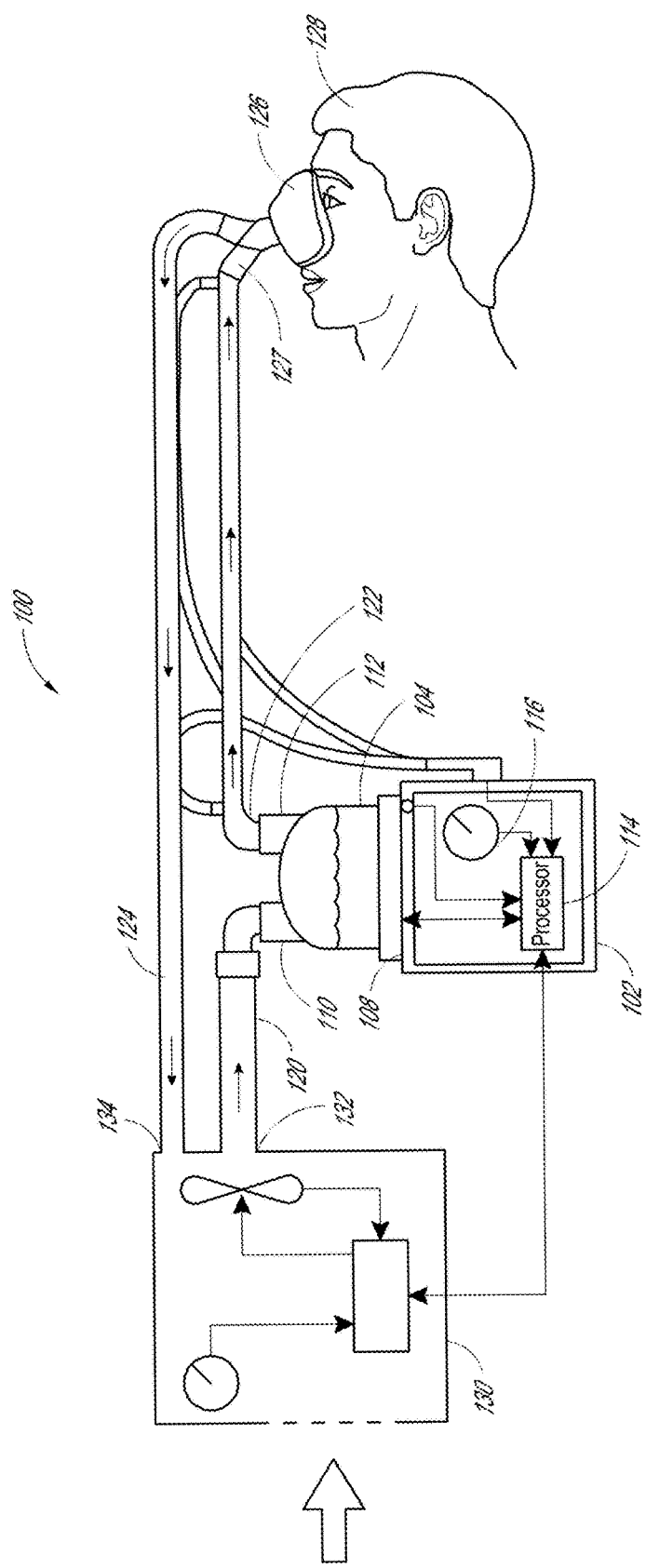
FIG. 1 illustrates an example embodiment of a humidification system.
Figure 3:
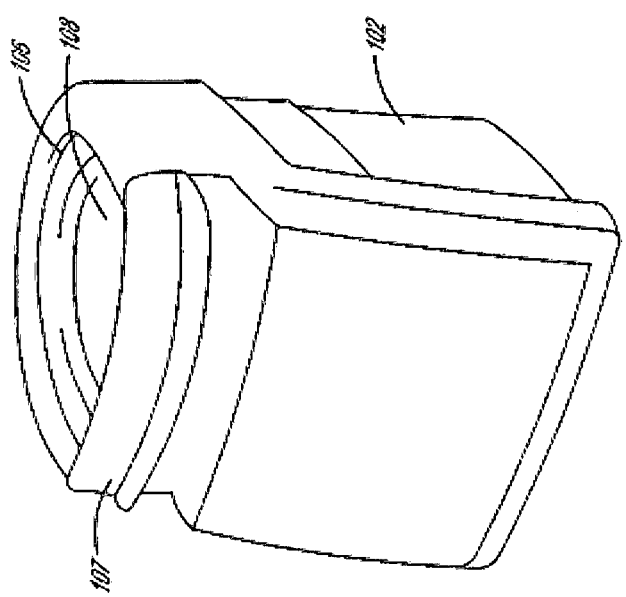
FIG. 3 illustrates an example embodiment of a heater base.

An example embodiment of a humidification system 100 can include a heater base 102, a humidification chamber 104, and a breathing circuit or breathing circuit assembly, for example, as shown in FIG. 1. In some embodiments, the system 100 further comprises a gases supply 130, for example, a ventilator or other suitable source of pressurized gases suitable for breathing or use in medical procedures. The heater base 102 can include a heater plate 108 (better shown in FIG. 3). In addition, the heater base 102 can comprise one or more processors 114, and one or more memories or other suitable storage components. In some embodiments, the heater base 102 also comprises a display that can provide information to and/or receive input from an operator.

In some configurations, the display can have a schematic to facilitate the operator making the desired connections, in some instances in a desired order. For example, the display can have a static image with lights (e.g., LED) under different regions that light in a sequence to encourage the desired connection order. In some configurations, the image can be formed on membranes that are back-screen printed behind a polyester or polycarbonate film with LEDs attached to or positioned adjacent to the film. In some configurations, the lights may begin the sequence when a switch is operated by insertion of a humidification chamber into the heater base or the like. Such configurations resolve any need for an operator to turn on the heater base to get the feedback on proper connection sequence. Other suitable arrangements also can be used.

The humidification chamber 104 generally comprises an inlet 110 and an outlet 112 and is configured to be installed on the heater plate 108 of the heater base 102. The humidification chamber 104 is further configured to hold a volume of a liquid, such as water. The chamber 104 can include an opening or port for the connection of a liquid conduit or feedset 118. The liquid conduit 118 can extend from the chamber 104, as shown in FIG. 2A. In some configurations, the liquid conduit 118 can connect to a spike for a water bag. In some configurations, the liquid conduit 118 can be integrally formed with or permanently coupled to the chamber 104. The spike can be coupled to the liquid conduit 118 via an adhesive, sonic welding, an interference fit, or any other suitable means. In some embodiments, the spike includes a vent. If the spike is inserted into, for example, a plastic, collapsible bag, the vent is plugged. However, if the spike is inserted into a rigid container, such as a glass bottle, the vent is open and allows air to enter the container to help reduce or prevent negative pressures in the container. The vent can include a filter that is permeable to gases but impermeable to liquids.

In use, the liquid conduit 118 conveys a liquid, for example, water, from a liquid source, such as a water bag, saline bag or the like, to the chamber 104. The heater plate 108 heats the chamber 104 and causes at least some of the chamber 104 contents to evaporate. In some embodiments, the humidification chamber 104 can include features to help reduce the likelihood of the level of liquid in the chamber 104 from exceeding a particular level. For example, the chamber 104 can include one or more floats 150 as shown in FIGS. 2B, 4A, and 4B. The floats rise and fall with the level of liquid in the chamber 104. When the liquid level reaches a certain level, the floats 150 obstruct or block the port that is connected to the liquid conduit 118 to stop or slow further ingress of liquid into the chamber 104. Other similar features also can be used. In a preferred embodiment, a plurality of floats 150 are used, each float adapted to stop the further ingress of liquid into the chamber 104. To this end, a second float provides a backup or safety mechanism, thereby further reducing the likelihood of the chamber 104 overfilling. FIG. 2B illustrates an example embodiment of such a chamber 104 having a primary float 250a and a secondary float 250b.

With reference again to FIG. 1, the breathing circuit assembly can include a supply conduit 120, an inspiratory conduit 122, and, in some configurations, an expiratory conduit 124. A gases supply end of the supply conduit 120 is configured to connect to an output 132 of the gases supply 130 and a chamber end of the supply conduit 120 is configured to connect to the chamber inlet 110 of the chamber 104. A chamber end of the inspiratory conduit 122 is configured to connect to the chamber outlet 112 of the chamber 104, and a user end of the inspiratory conduit 122 is configured to connect to the user 128 via an interface 126, for example. A user end of the expiratory conduit 124 is configured to connect to the interface 126, and a gases supply end of the expiratory conduit 124 is configured to connect to a return 134 of the gases supply 130. The user ends of the inspiratory conduit 112 and expiratory conduit 124 can be connected to the interface 126 via a Y-piece 127, for example but without limitation.

In use, gases flow from the gases supply 130 through the supply conduit 120 and into the chamber 104 via the inlet 110. The gases are humidified within the chamber 104 and exit the chamber 104 through the outlet 112. The user inhales humidified gases supplied through the inspiratory conduit 122, and exhales into the expiratory conduit 124. The inspiratory conduit 122 and/or expiratory conduit 124 can include a heating element, for example, a heating wire, to help maintain the gases at a desired temperature and to reduce the likelihood of significant condensation formation in the conduits.

Before use, an operator, such as medical personnel, must correctly connect the various components to set up the system 100. Because of the variety of components and number of connections that must be made, set-up of the system 100 can be a complex process that requires special training to complete properly. The humidification system 100 can include various features as described herein to simplify the set-up process and reduce the likelihood of an incorrect set-up. In some embodiments, certain usability features advantageously can help reduce the total number of steps and time required during the set-up process. Some features described herein also can help make set-up more intuitive for the user, which can reduce the need for specialized in-service training.

To begin set-up, the operator installs the humidification chamber 104 on the heater base 102 by sliding the chamber 104 onto the heater base 102 under a rim edge 106 (shown in FIG. 3) that helps hold the chamber 104 in place. The heater plate 108 can be spring loaded in some configurations such that the base of the chamber 104 presses downward upon the heater plate 108 and a protruding portion 105 of the chamber 104 can be captured between the heater plate 108 and the rim edge 106. Preferably, a guard 107 along a front portion of the rim edge 106 is depressed to enable the lower portion of the chamber 104 to access the heater plate 108 and then the guard 107 reverts to a non-depressed position once the chamber 104 is installed. In some configurations, the forwardmost portions of the rim edge 106 (e.g., the portions of the rim edge 106 that define an opening for insertion of the chamber 104) are configured with a raised or enlarged opening 109 that ramps downward. The opening 109 preferably comprises a lower surface that is elevated above an upper surface of the non-depressed guard 107. In such a manner, the openings 109 provide a visual clue to the operator that the protruding portion 105 can be inserted into the opening. Further insertion of the chamber 104 into the opening causes the guard 107 to be depressed and facilitates full insertion of the chamber into the heater base and can help guide the chamber 104 into place. Thus, the visual details can indicate to the operator that the chamber 104 slides into place under the rim edge 106. This can also help inform the operator that the guard 107 can be depressed to later remove the chamber 104 from the heater base 102. Preferably, the chamber 104 has details to depress the guard 107 when the operator attempts to remove the chamber 104 from the heater base 102. Moreover, by providing an uneven upper surface to the rim edge 106, the operator is less likely to believe that the chamber 104 should be placed atop the rim edge 106, resulting in poor thermal conductivity, because such a placement will lead to an uneven chamber 104.

Humidification chambers, such as the chamber 104, often have a generally rounded shape with generally smooth sides, which can make it difficult for the operator to hold the chamber 104 during set-up and installation. In setting up the humidifier, the chamber 104 will be grasped and then slid into position on the heater base 102, as described above. Therefore, as shown in FIG. 4D, the chamber 104 can include grips 168 to advantageously allow the operator to hold the chamber 104 more easily during installation. In some embodiments, for example as illustrated in FIG. 4D, the grips 168 are positioned at particular locations on the chamber 104 to help guide the operator to correctly orient the chamber 104 when sliding the chamber 104 onto the base 102. In some embodiments, the grips 168 extend partially or completely around the chamber 104. The grips 168 can include one or more of, for example, depressions or cavities on the chamber 104 surface, vertical fins, a textured surface, and/or a handle. In the illustrated configuration, a sidewall of the chamber includes recesses that extend inwardly toward the chamber. The recesses can include ribs or the like to enhance the ability of a user to grip the chamber by the recesses. The recesses can be positioned along a forward facing surface. In some configurations, the upwardly extending ports of the humidifier chamber can include openings that face rearward while the recesses are concave into the humidifier chamber and facing forward. The forward facing grips help orient the chamber for installation. In some configurations, the recesses extend only partially up the full height of the chamber. In some configurations, the recesses are opposed to each other such that a gripping force can be applied with fingers and thumb by the user.

With reference to FIG. 4A, the humidification chamber 104 can be packaged with port caps 160 covering the inlet 110 and the outlet 112. The port caps can seal or generally enclose the chamber 104 during shipping and storage. The port caps 160 can include legs 162 that extend into the inlet 110 and the outlet 112 and that restrain the float 150 in position for shipping. In some configurations, the liquid conduit 118 can be wound around, and can be contained by, a winder 166 provided on the chamber 104. During set-up, after the humidification chamber 104 is installed on the heater base 102, the port caps 160 can be removed, preferably prior to the liquid conduit 118 being unwound and connected to the liquid source via a spike 164. Once the spike 164 connects to the liquid source, liquid will begin filling the chamber 104. However, if the liquid conduit 118 is connected to the liquid source before the port caps 160 are removed, there is a risk of the chamber 104 over-filling because the float 150 is still restrained and cannot function to slow or stop the flow of liquid into the chamber 104.

To reduce the likelihood of overfilling, in some embodiments, the chamber 104 is packaged with the liquid conduit 118 captured between the inlet port 110 and the outlet port 112 of the chamber 104 and the port caps 160. The liquid conduit 118 can further be somewhat obscured from the operator until the port caps 160 have been removed. Preferably, however, the presence of the liquid conduit 118 below the port caps 160 can be viewed with the port caps 160 in position, which leads the operator to remove the port caps 160 to access the liquid conduit 118. Furthermore, removal of the port caps 160 preferably results in the unwinding or unfurling of the liquid conduit 118. This packaging arrangement also reduces or eliminates any need for a winder 166 to contain the liquid conduit 118 and the set-up steps of removing the winder 166 from the chamber 104 and unwinding the liquid conduit 118 from the winder 166. In some embodiments, the spike 164 and/or liquid conduit 118 are free-floating and not constrained by a winder 166 or the port caps 160. This can help reduce possible operator confusion as to whether the liquid conduit 118 should be unwound during set-up. In some arrangements, the spike 164 freely hangs exposed to further encourage removal of the port caps 160. In some configurations, the spike 164 is partially exposed and partially captured by the port caps 160 which encourage removal of the port caps 160 to access the spike 164.

Figure 4C:
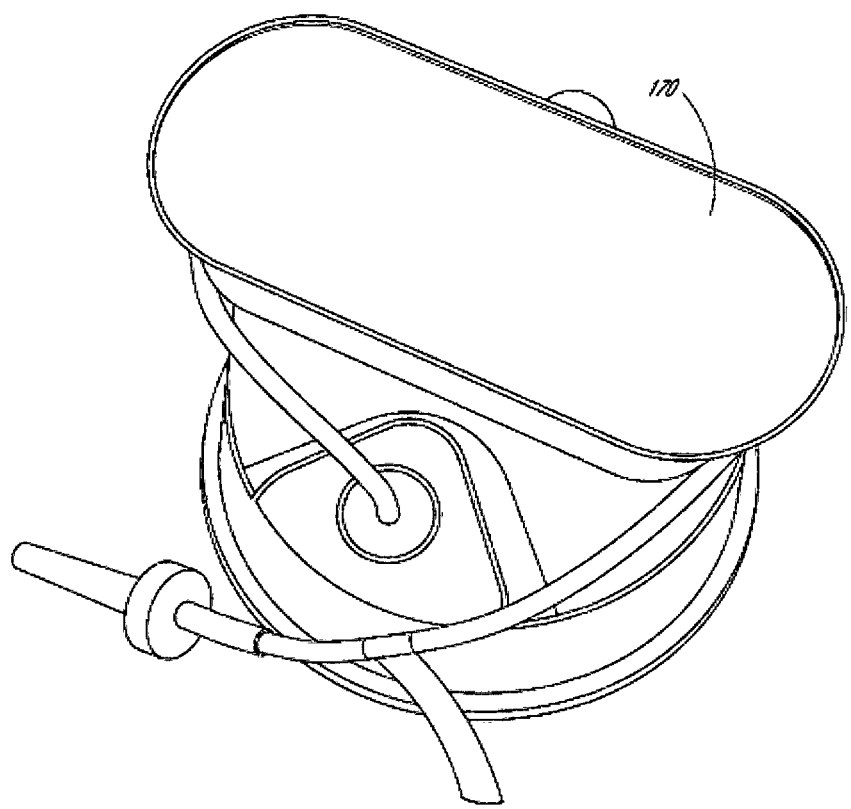

Additional features can help reduce the likelihood of operators mistaking the port caps for operational components of the system intended to remain in place during use. For example, an alternate port cap 170 can include a single flat surface spanning the top of both ports and simple side faces encircling the ports and, optionally, the liquid conduit 118 as shown in FIGS. 4B and 4C. This design can give the port cap 170 the appearance of a lid to be removed from the chamber 104 before use. The port cap 170 can also include a lip detail around some or all of a perimeter of the flat top surface that the operator can grip for removal. The flat top surface provides a surface for an optional instruction label or a label having an image of, for example, a trash can to indicate to the operator that the port cap 170 is supposed to be removed and discarded. In some configurations, the port caps can be formed of a material or have a coloration that will confirm an instinct to dispose of the port caps.

With reference to FIG. 4D, another example embodiment of a port cap 170 that can be used with a winder 166 includes a cap body 172 and a float retainer 174 having a tab or pull loop 176 and legs 162 that extend into the inlet 110 and the outlet 112 to restrain the float 150. The cap body 172 can be formed to be at least partially translucent or substantially transparent to reveal the conduit contained within the cap body 172. The cap body 172 can include an arrow and/or other visual or other indicators to direct the operator on the correct direction for insertion of the chamber 104 on the heater base 102. In some embodiments, the cap body 172 can include a label that includes instructions for set-up of the chamber to increase the likelihood of a correct or desired sequence of set-up steps being followed by people performing set-up operations. In some embodiments, the float retainer 174 is separate from the cap body 172 and can be removed from the chamber 104 before the cap body 172 as shown in FIG. 4E. Removal of the cap body 172 exposes the winder 166, as shown in FIG. 4F. Alternatively, the float retainer 174 can be integrally molded with or coupled to the cap body 172 so that both components are removed simultaneously, for example, by pulling on the pull loop 176. Both embodiments advantageously ensure that the float retainer 174 is removed when the winder 166 is exposed so that the float 150 is unrestrained before the liquid conduit 118 is connected to the liquid source. In some embodiments, the winder 166 is coupled to the chamber 104 with clips or other features that connect to, clip to or otherwise engage the chamber ports. As shown in FIG. 4F, the liquid conduit 118 can extend from a liquid inlet 117 in the chamber 104, around the winder 166, and into the winder 166 through a vent 167 to couple to the spike 164, which can be seated within the winder 166 as shown in the illustrated embodiment. In the illustrated embodiment, the cap body 172 is sized and shaped to also cover the liquid conduit 118 when in place for shipping and/or storage. In some configurations, the winder 166 includes features to secure the spike in a horizontal position (e.g., a shipping position) and in a non-horizontal or vertical position (e.g., a testing position). For example, the winder 166 can have a generally oval shape and can include a longitudinal receptacle 186 within the winder 166 configured to receive and/or to secure the spike in a horizontal shipping position. The winder 166 can also include a generally circular receptacle 188 configured to receive a grip portion 190 of the spike 164 (shown in FIG. 4J) so that the spike 164 can be placed in a generally vertical position for testing. The liquid conduit 118 can be secured in the liquid inlet 117 with an adhesive such as glue or any other suitable technique. A tubing holder 119 can help secure the liquid conduit 118 to a portion of the winder 166 or to the top of the chamber 104 and help route the liquid conduit 118 from the liquid inlet 117 to the winder 166. In some embodiments, the operator can remove the spike 164 from the winder 166 and unwind the liquid conduit 118 from the winder 166 to connect the spike 164 to the liquid source. In some embodiments, the operator can remove the winder 166 from the chamber 104 and discard the winder 166 after unwinding the liquid conduit 118.

Additional embodiments of liquid conduit 118 packaging are shown in FIGS. 4G1-4G2 and 4H1-4H2. In both illustrated embodiments, the liquid conduit 118 is wound into a looped configuration, for example, by winding the liquid conduit 118 around a jig. In some embodiments, a label 218 is attached to the liquid conduit before winding and used to secure the liquid conduit 118 in the looped configuration. In the embodiment of FIG. 4G1-4G2, the looped liquid conduit 118 is placed within a foldable card 178 coupled to the top of the chamber 104 as shown in FIG. 4G1. The card 178 can be made of cardboard, plastic, a flexible material, or any other suitable material, and a bottom portion 178a can be secured to the chamber 104 with an adhesive and/or by cutouts 280 configured to be placed around the chamber inlet and outlet ports. A top portion 178b of the card 178 can be folded over the bottom portion and secured with cutouts configured to be placed around the chamber inlet and outlet ports and/or with port caps 160, for example as shown in FIG. 4G2. In some embodiments, the spike 164 is secured to a base of the card 178 between the top and bottom portions via a slot or clip. The bottom portion 178a of the card can include a slit 282 to accommodate the liquid conduit 118 extending between the card 178 and the liquid inlet 117. In some configurations, the looped conduit can be placed width-wise on the card. In the embodiment shown in FIGS. 4H1-4H2, the looped liquid conduit 118 is placed in a molded cavity 111 on the top of the chamber 104 and protected by a tube enclosure 179, which can include port caps 160. A bottom surface of the tube enclosure 179 can include a feature to secure the spike 164. In some embodiments, a label with branding, instructions, and/or other information can be attached to the tube enclosure 179, the card 178 (e.g., the top portion 178b or the card 178). In other words, in some configurations, one or more of the card (e.g., the top portion 178b of the card 178) and the tube enclosure 179 can incorporate one or more surfaces that can be used for instructions (e.g., unpacking instructions, set-up instructions or the like), labels or warnings. In some configurations, the card 178 can include sequential instructions that increases the likelihood of a correct or desired sequence of set-up steps being followed by people performing set-up operations. For example, the card 178 can be provided with sequential or staggered steps to follow. In some configurations, the card 178 or another component can explain only steps that involve exposed or accessible components.

Figure 4I:
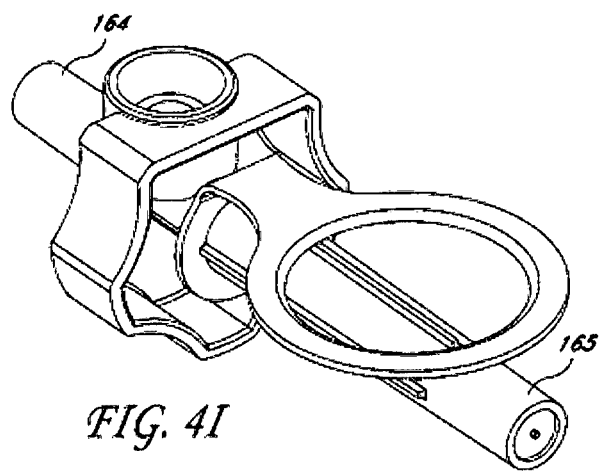
FIG. 4I illustrates an example embodiment of a spike including a sheath.
Figure 4J:
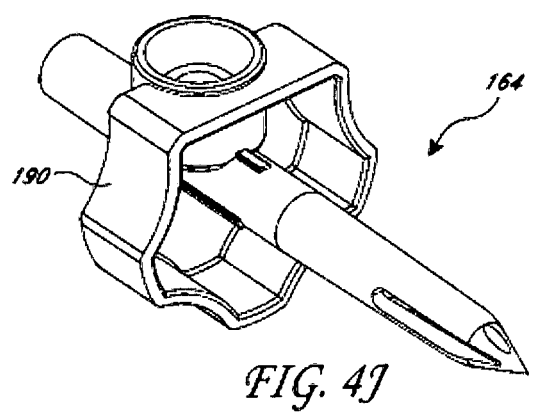
FIG. 4J illustrates the spike of FIG. 4I without the sheath.

As shown in FIGS. 4F and 4I, the spike 164 can be packaged with a spike cap or sheath 165 that the operator removes before use, as shown in FIG. 4J. The sheath 165 can include a tab or a similar feature for easier removal of the spike 164 from the winder 166 and/or of the sheath 165 from the spike 164. In some configurations, the cap is not connected to any other member such that the operator knows to remove the cap. Labels also can be used to instruct the operator on how to set up the liquid conduit 118 and liquid source. Typically, humidification systems 100 utilize water to humidify gases passing through the humidification chamber 104. To indicate to the operator that the spike should be connected to a water bag rather to another type of liquid, such as saline, the liquid conduit 118 and/or the chamber 104 can include labels, e.g., reading "$H_2O$." Preferably, any such visual indicator, including the label, is positioned closer to the spike than to the body of the chamber when the conduit is stretched outward. The label on the liquid conduit 118 can also help draw the operator's attention to the water spike 164, which may not be obvious to the operator when concealed by the spike cap. The chamber 104 can also include labels to indicate the appropriate water level.

In some configurations, a spike can be secured to tubing using any suitable technique. For example, in some configurations, the spike can be secured to the tubing using adhesives, sonic welding, interference fit or the like. A label then can be attached to the tubing. In some configurations, the label can be loosely looped over the tubing and can include a sticky end (e.g., exposed adhesive). In some configurations, the label can be positioned closer to the spike than to another end of the tubing. The tubing can be wound around a jig or the like and secured in a looped configuration using the label (e.g., using the sticky end to tack the end of the label to another portion of the label). When winding the tubing, the ends preferably are provided with enough slack to connect the tubing and spike to the chamber. The end without the spike can be secured to the chamber using any suitable technique. In some configurations, the end without the spike can be inserted into a water inlet hole of the water chamber and fixed with glue or the like. The ends of the loop of tubing can be placed over or between the inlet and outlet ports of the chamber. The spike can be secured into a receptacle. In some configurations, the receptacle can be formed in, or secured to, a portion of the chamber. In some configurations, the spike is secured to the chamber with the point extending away from the chamber for testing. Testing can be conducted on the assembled chamber. After testing, the spike can be removed from the chamber and the spike and tubing can be secured in any suitable manner for shipping, including those set forth above.

The humidification system 100 can include reusable temperature and/or flow probes at or near the humidification chamber 104. For example, a flow sensor can be positioned in the chamber inlet 110 to sense the flow rate of the gases entering the chamber 104 from the gases supply 130. A temperature sensor can be positioned in the chamber inlet 110 to sense the temperature of the gases entering the chamber 104 from the gases supply 130. A temperature sensor can be positioned in the chamber outlet 112 to sense the temperature of the humidified gases leaving the chamber 104. A flow sensor can also or alternatively be positioned in the chamber outlet 112 to sense the flow rate of gases leaving the chamber 104 to be delivered to the user.

Figure 5A:
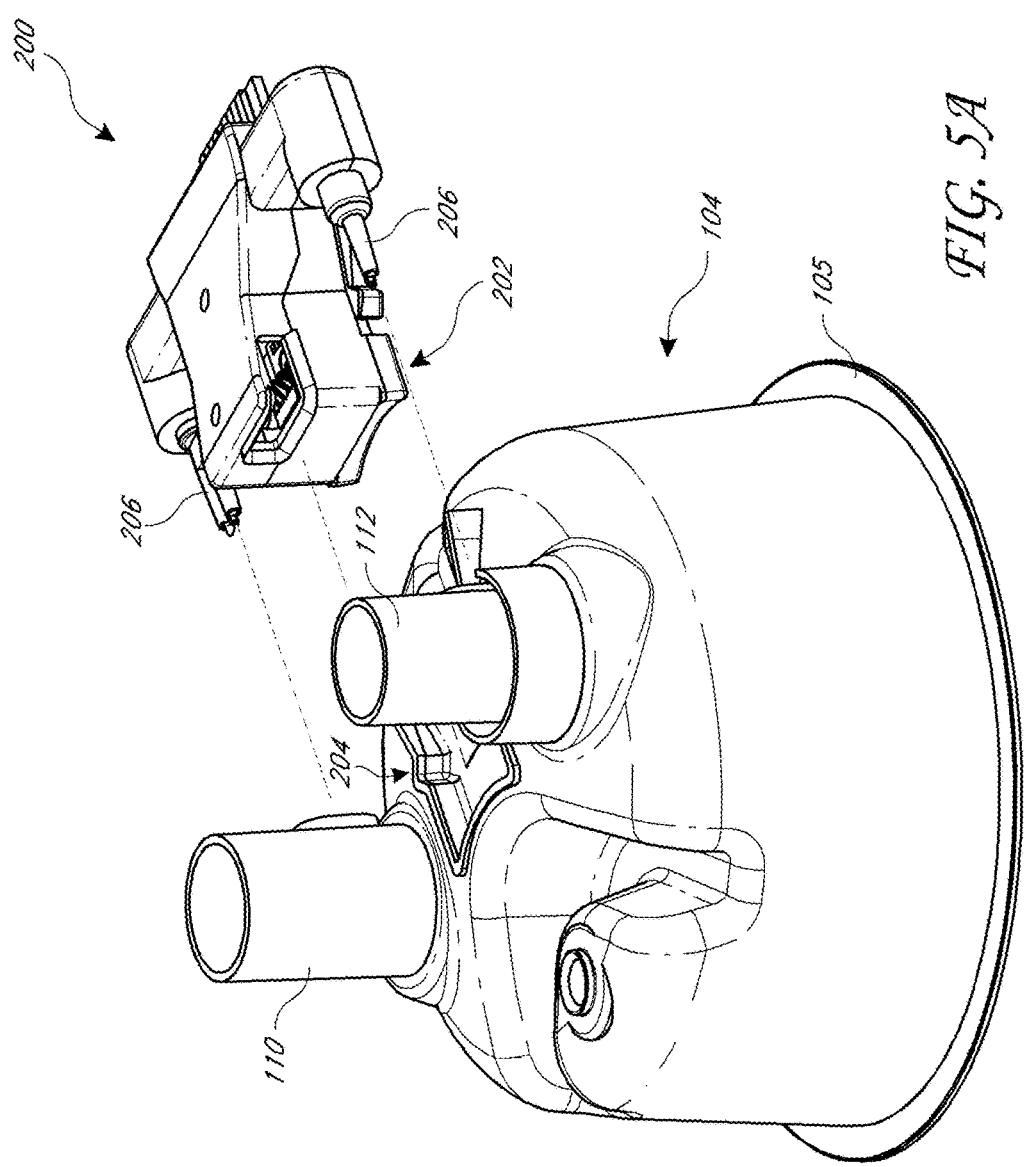
FIG. 5A illustrates an example embodiment of a sensor cartridge module and humidification chamber.
Figure 5B:
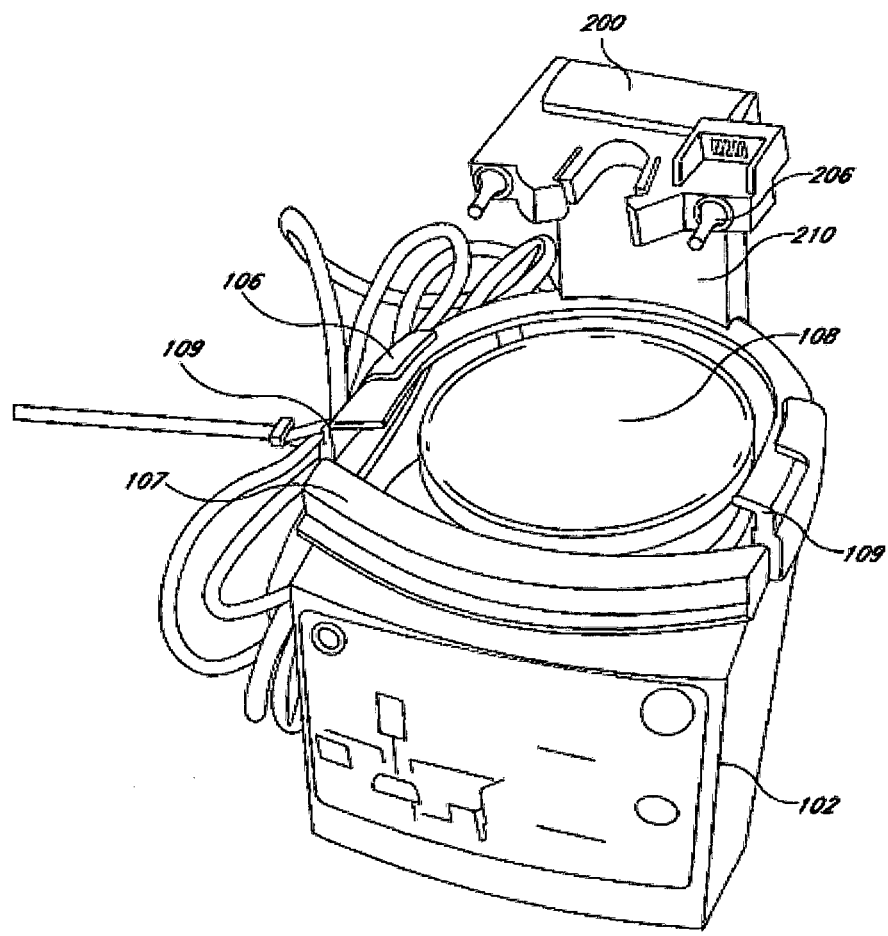
FIG. 5B illustrates an example embodiment of a sensor cartridge module coupled to a heater base.
Figure 5C:
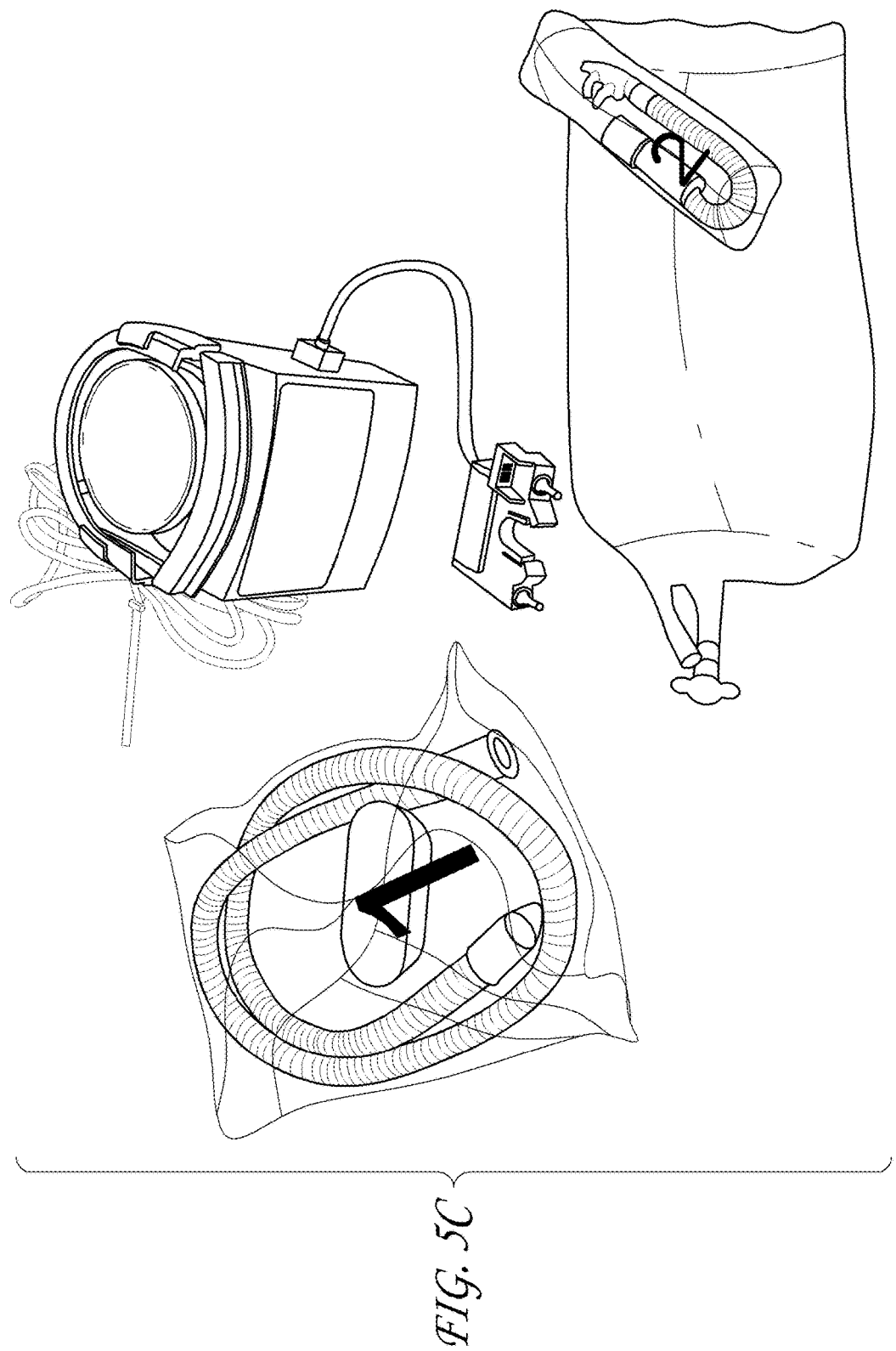
FIG. 5C illustrates an example embodiment of a sensor cartridge module connected to a heater base with an electrical cable.

In some embodiments, reusable temperature and/or flow sensor probes 206 can be integrated into a sensor cartridge module 200, as shown in FIG. 5B. FIG. 5C shows the sensor cartridge module 200 connected to the heater base with an electrical cable. The sensor cartridge module 200 in FIG. 5B, however, is mechanically and electrically connected to the heater base 102 via a spine 210 and can therefore provide for the transfer of power to the sensors while also providing a mounting location for the sensors, for example but without limitation. In some configurations, the spine 210 and the port cap can have an interfacing configuration such that movement of the chamber with the port cap in position toward the spine during mounting of the chamber to the heater base will cause the spine to lift the port cap from the chamber. Such a configuration increases the likelihood of the operator removing the port cap from the chamber. Other suitable configurations also can be used.

Figure 6:
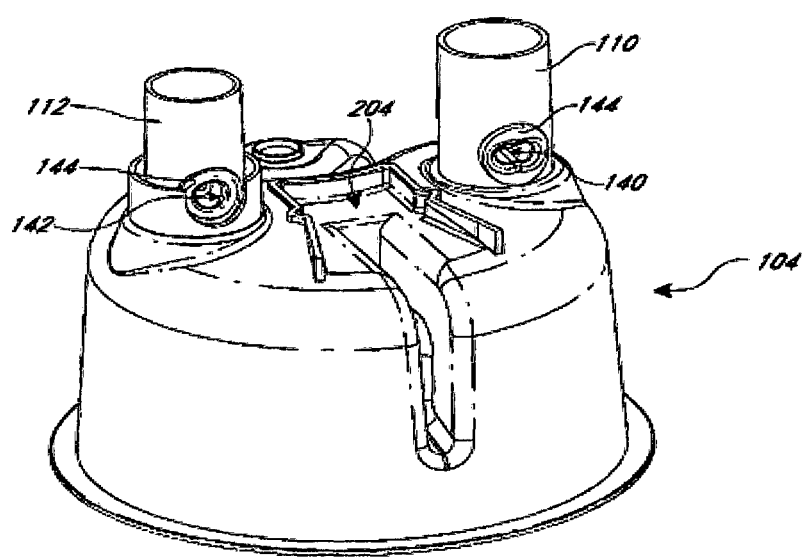
FIG. 6 illustrates an example embodiment of a humidification chamber.

The sensor cartridge module 200 also allows for the transfer of data between the sensors and the processor 114 in the heater base 102. The chamber inlet 110 and outlet 112 can have apertures 140, 142 therethrough, for example as shown in FIG. 6. Probe membranes or grommets 144 sized and shaped to receive the temperature and/or flow probes 204, 206 can be positioned within and pneumatically seal the apertures 140, 142. In the configuration of FIG. 5B, the operator is encouraged to position the chamber base below the rim edge 106 because otherwise the probes attached to the spine will not properly align with the respective apertures.

Correct insertion of the chamber 104 into the heater base 102 can automatically position the sensor probes 206 within the apertures 140, 142 of the chamber inlet 110 and outlet 112. This can advantageously allow for an easier set-up compared to separate reusable sensors, which must be manually inserted and electrically connected to the heater base 102, and reduce the possibility of improper electrical connection, improper pneumatic sealing and/or assembly. The probe membranes 144 protect the probes from direct contact with the gases passing into and out of the chamber 104. The probes therefore can be reused without requiring cleaning and storage of the probes 206 and disconnection and reconnection of wires between uses.

To help guide the operator through installation of the chamber 104 on the heater base 102 and proper connection with the sensor cartridge module 200, the chamber 104 and sensor cartridge module 200 can include lead-in features, such as corresponding male and female connections. For example, one or more of the base 102 and the cartridge module 200 can include structures that mate with structures 201 on the chamber 104. In the configuration of the chamber 104 shown in FIG. 4F, the structures 201 are recessed portions. Thus, the chamber 104 can have a shorter vertical height on the portion closest to the housing of the heater base 102 when mounted while the chamber 104 has a taller vertical height on the portion that is positioned away from the cartridge module 200. Such a configuration reduces the likelihood of the chamber being inserted into the base 102 backwards, which can result in damage to the sensors. Thus, the cooperating formations greatly increase the likelihood that coupling of the chamber 104 to the base 102 is only achieved in a correct rotational orientation of the chamber 104. Moreover, the cooperating structures can provide visual cues to the proper rotational orientation of the chamber 104. The cooperating structures can be a male on the base and a female on the chamber, a female on the base and a male on the chamber, or any combination of male and female portions on the base and the chamber.

By way of another example, the sensor cartridge module 200 can include a central male projection 202 configured to slide into a female recess 204 in the chamber 104. Alternatively, the chamber 104 can include a male projection configured to slide into a center of the sensor cartridge module 200. Preferably, the female recess 204 is configured in such a manner that only one orientation of the chamber relative to the male projection 202 is possible. Any other configuration or snap together assembly can be used. In some configurations, the chamber 104 can include a chamfered or angled edge or protrusion 205 on the lateral sides, for example, but without limitation. These protrusions 205 can cooperate with a structure of the base 102 or on the cartridge module 200. The cooperation preferably helps to pull or encourage the chamber 104 into a fully seated position relative to the base 102. Thus, the protrusions 205 and the cooperating structures provide another example of structures that can orient and properly position the sensor probes 206 relative to the chamber. These means for orienting the chamber relative to the heater base also advantageously aid proper positioning of the sensor probes 206 within the chamber ports. Advantageously, when the chamber 104 docks on the sensor cartridge module 200, the sensor probes can be automatically inserted into the chamber ports to the appropriate distance or depth. In other words, the risk of the probes 206 not fully inserting to the ports of the chamber 104 can be reduced or eliminated. Preferably, the connection between the sensor cartridge module 200 and the chamber 104 is generally horizontally (e.g., parallel with an upper surface of the heater plate).

In some configurations, the chamber can have recess that accommodates a protrusion from the spine or other portion of the heater base. Such a configuration can help guide the chamber into position on the heater base in a desired rotational orientation. In some configurations, rather than being translated into position, the chamber can be rotated into position on the heater base. For example, slots can be provided with posts that can slide vertically downward into the slots such that rotation of the chamber will position the posts under the rim edge 106. In some configurations, if the sensor cartridge module 200 is mounted to the chamber before the chamber is mounted to the heater base, rotation of the chamber can establish an electrical connection between components mounted to the chamber (e.g., sensors) and the heater base. Rotation of the chamber also defines a horizontal connection direction. Other configurations also are possible.

Some humidification systems 100 also include temperature and/or flow rate sensors at various locations in the breathing circuit to monitor conditions of the gases as they travel through the system 100 to and from the user 128. Some such systems include reusable temperature sensors at or near a user end of the inspiratory conduit 122 to ensure the gases reaching the user 128 are at an appropriate temperature. Because the various conduits of the circuit are typically disposable, reusable temperature sensors must be separately coupled to the inspiratory conduit 122 during set-up and must further be connected to the heater base 102 for power and data transfer. The user may forget to connect the sensor and/or sensor cable entirely, or may inadvertently fail to fully insert the sensor into the inspiratory conduit 122, which can skew the sensor data. According to some embodiments of the present disclosure, a single-use user end temperature sensor and associated sensor cable can be integrated with the inspiratory conduit 122. This can advantageously eliminate the steps of connecting a separate sensor and sensor wires during set-up, as well as the steps and time required to clean and store reusable sensors.

In some embodiments, the sensor cartridge module 200 can allow for power and data transfer between the heater base 102 and the inspiratory conduit 122 user end temperature sensor and an inspiratory conduit 122 heater wire. The inspiratory conduit 122 chamber end connector can include an electrical connection for coupling to a corresponding connection on the sensor cartridge module 200. This provides a simpler alternative to using a reusable sensor cable to provide an electrical connection between the user end temperature sensor and the heater base 102 and a reusable heater wire adapter cable to provide an electrical connection between the inspiratory conduit 122 heater wire and heater base 102. The user end temperature sensor and heater wire can be coupled to the electrical connection of the inspiratory conduit 122 chamber end connector via wires that are integrated in or run alongside the exterior of the inspiratory conduit 122.

If the expiratory conduit 124 includes a heating element, e.g., a heater wire, the heating element is typically powered via an electrical cable connecting the heating element to the heater base 102. To help simplify set-up, both ends of the heating element electrical cable can have plugs of the same design. Corresponding sockets can be located on the heater base 102 and the expiratory conduit 124 gases supply end connector. Either end of the heating element electrical cable can be coupled to either the expiratory conduit 124 gases supply end connector socket or socket of the heater base 102. The operator therefore does not need to spend excess time determining the correct orientation for the heating element electrical cable.

Figure 7A:
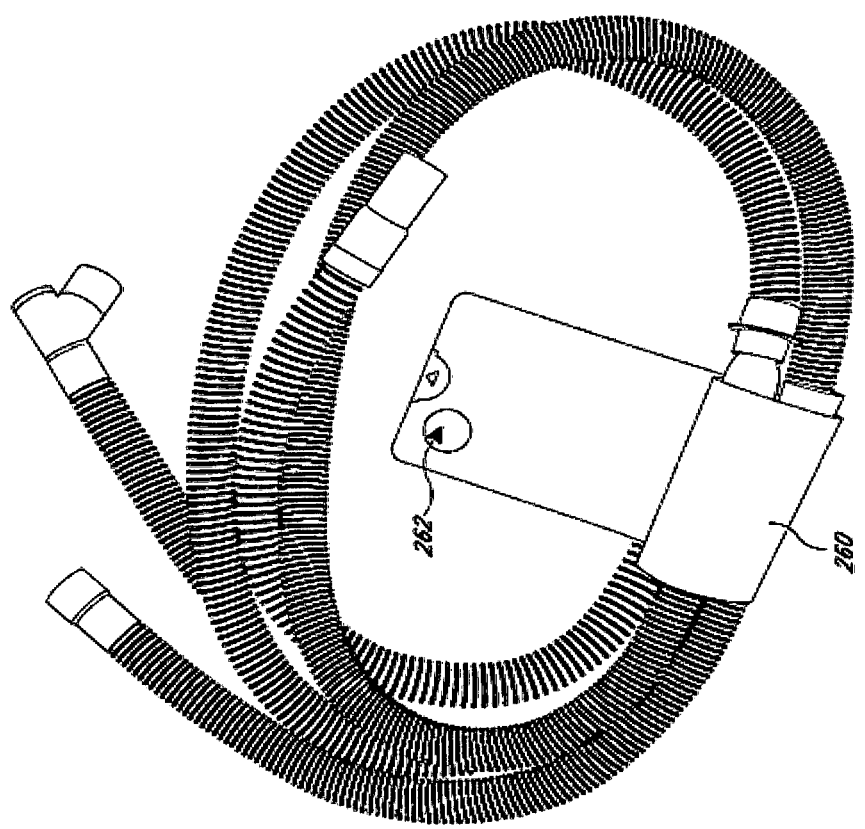
FIG. 7A illustrates an example embodiment of breathing conduits as packaged.

As explained herein, the breathing circuit can include multiple conduits requiring multiple connections to the chamber 104, user 128, and/or gases supply 130. The length of the conduits can make them difficult to handle and control during set-up, increasing the risk of the conduits being accidentally dropped on the ground and possibly contaminated. To improve handling and control during removal from packaging and set-up, the circuits can be packaged and held together in a looped configuration with a circuit sleeve 260 as shown in FIG. 7A. In some embodiments, the sleeved conduits can be packaged in a protective plastic bag or the like. In some embodiments, the circuit sleeve 260 is made of cardboard or a thin plastic sheet, although other materials are also possible. The circuit sleeve 260 can be looped or wrapped around the conduits and closed or held together with, for example, staples, tape, and/or an adhesive, e.g., glue. In some embodiments, ends of the sleeve 260 have interlocking features to close the sleeve 260 around the conduits, for example, interlocking slits or a tab and corresponding slot. The conduits can also be held in a looped configuration by tape, rubber bands, straps, or the like.

The looped configuration can advantageously allow the operator to hang the conduits on, for example, the forearm, the heater base, or another object to free up the operator's hands for other set-up tasks. In some embodiments, the circuit sleeve 260 includes a hole 262 that can be used to hang the looped conduits on a hook, for example, a hook used to hang the water bag or an I.V. bag, as an alternative to placing the conduits on other hospital surfaces that can increase the risk of contamination. The circuit sleeve 260 can be positioned on the conduits to conceal selected conduit connectors and help direct the operator's attention to visible conduit connectors, which can be the connectors that should be connected first during the set-up process. If the operator makes the appropriate connections with the visible conduit connectors before removing the circuit sleeve 260 to expose the remaining connectors, the operator will have a reduced number of possible connections, thereby making it easier and more likely to correctly complete the set-up. In some embodiments, the circuit sleeve 260 can include set-up instructions, in writing and/or pictures, to help direct a preferred set-up sequence to achieve the correct set-up. The circuit sleeve 260 can also be positioned on the conduits to cover and/or isolate any sharp edges or corners (e.g., portions of the connectors) to help reduce the possibility of damage to, for example, other circuit components, the chamber, and/or the packaging material during shipping or the like.

Figure 7B:
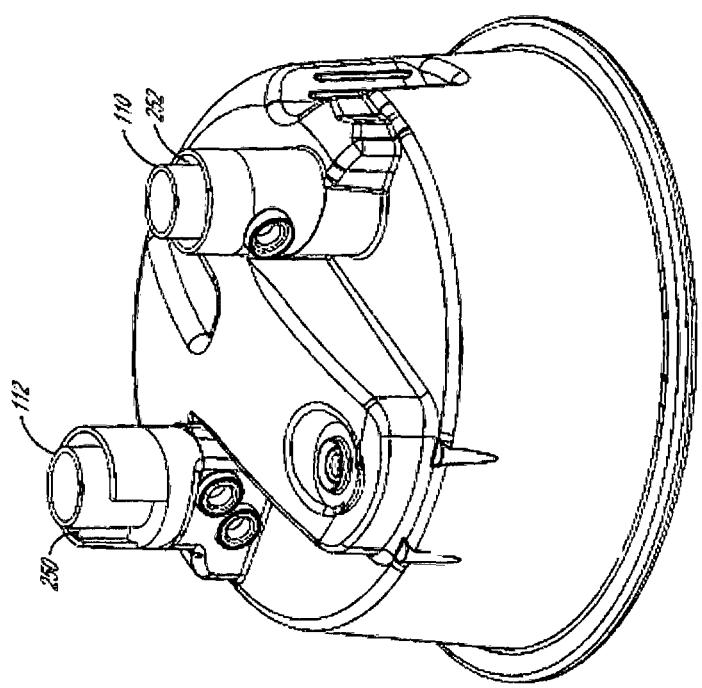
FIG. 7B illustrates an example embodiment of a humidification chamber with features to promote proper connections.
Figure 8B:
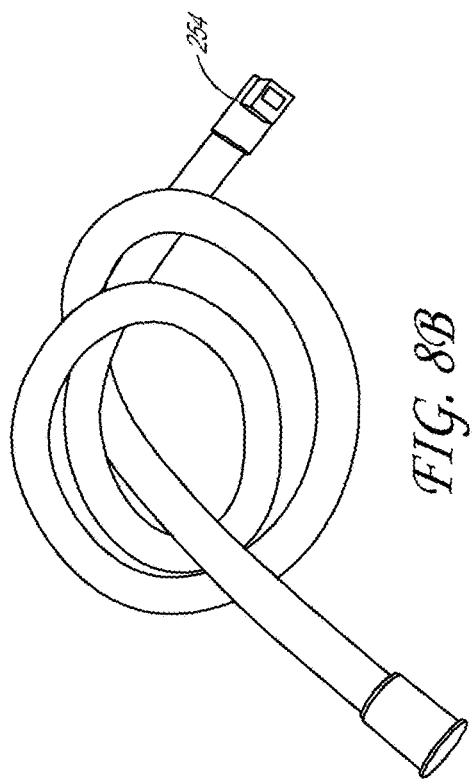
Figure 8A:
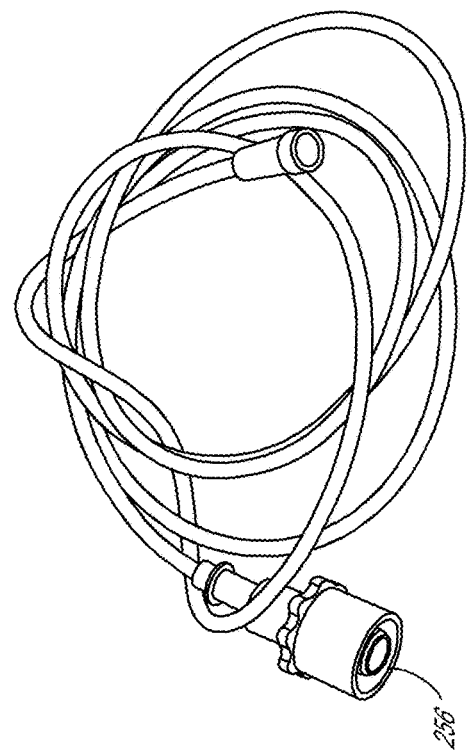
Figure 8C:
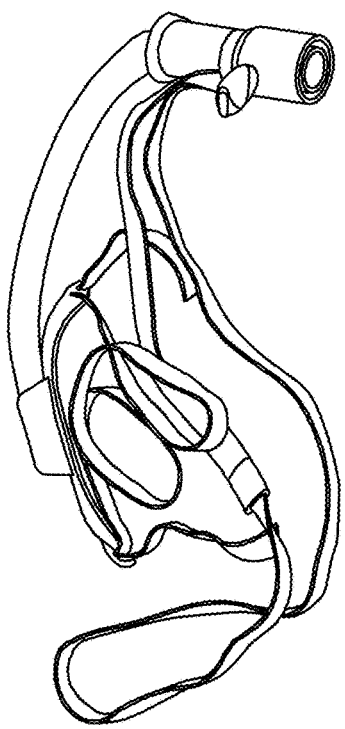

To help reduce the likelihood of incorrect connections during set-up, the conduit connectors, chamber inlet 110 and outlet 112, gases supply output 132 and input 134, interfaces 128, and/or Y-piece 127 can have varying diameters to help prevent incorrect connections from being made. In some embodiments, some or all of the connections can include details, such as rib details, that allow the appropriate components to be connected, but inhibit improper connections. For example, the chamber outlet 112 or inspiratory conduit port can include a rib detail 250 circumferentially surrounding the port 112 as shown in FIG. 7B. The inspiratory conduit chamber connector can include a corresponding rib detail 254 configured to engage the chamber outlet port rib detail 250 as shown in FIG. 8B. The chamber inlet or supply conduit port can similarly include a circumferential rib detail 252 to engage a corresponding rib detail 256 on the supply conduit chamber connector as shown in FIG. 8A. Other components, such as an inspiratory tube user end connector, expiratory tube user end connector, expiratory tube gases supply end connector, and/or supply conduit gases supply end connector can include outwardly extending rib details. In some configurations, different diameters can be used to make it difficult if not impossible to physically connect the wrong conduit to the wrong port. In addition, as described above, it is possible to form each end of each hose to have a unique configuration to help reinforce the desired connections. Other configurations are also possible.

In some embodiments, various components can be color coded to help guide the operator through the set-up process and help reduce the likelihood of incorrect connections. For example, the supply conduit 120 chamber end connector and chamber 104 inlet 110 port can be similarly colored to a first color, for example, green, to indicate to the operator that those two components are intended to be connected. Similarly, the inspiratory conduit chamber end connector and chamber outlet port can be color-coordinated to a second color, for example, blue. For a dual-limb circuit, the interface 126 and/or Y-piece 127 can be color-coordinated to a third color, for example, grey. For a single-limb circuit, the interface and the inspiratory conduit patient-end connector can be color-coordinated to a fourth color, for example, blue. The sensor cartridge module 200 temperature and flow probes 206 can be color-coordinated with probe membranes 144, for example turquoise. An adapter cable and plugs for the expiratory conduit heating element can be color-coordinated with sockets on the expiratory conduit gases supply end connector and heater base 102, for example, yellow. The components intended to be discarded during set-up, for example, the port caps 160, 170, winder 166, a Y-piece cap, and/or a cap for the water spike 164 can be colored similarly, for example, semi-transparent yellow or orange. Preferably, the cap for the water spike 164 is transparent, translucent or otherwise configured with slots, gaps, holes or the like to indicate to the operator that the spike is positioned within the cap. The supply conduit gases supply end connector and expiratory conduit gases supply end connector can be color-coded, for example, pink. In some embodiments, the conduits themselves can be differentiated through color. For example, the supply conduit 120 can be green, the inspiratory conduit 122 can be blue, and the expiratory conduit 124 can be white. In some embodiments, colors may be selected so that operators with reduced color recognition (such as red-green color blindness) are still able to differentiate the different components. In some arrangements, where an order is preferred, the color coding to be that over color mixing (e.g., red for first connections, orange for second connections, yellow for third connections, green for fourth connections and blue for fifth connections, for example but without limitation). Thus, patterns can be used to encourage proper progression as well as proper connections. In such configurations, LED, lights or color filters over lights can be used to show the color of the connections on the electric display or the colors can simply be shown on a display screen. Of course, other configurations and color palettes are also possible. In some embodiments, user instructions and/or errors can refer to the different components by their color.

In addition to or instead of color-coordinating the various components, the components can include corresponding symbols and/or text to indicate parts intended to be connected together. In some configurations, the first connections can be labeled "1" or "A" with the second connections being labeled "2" or "B," by way of example. In some embodiments, one or more of the conduits can include labeling indicating the proper direction of gas flow through the conduit in use. For example, the supply conduit 120 can include one or more arrows and, optionally, text similar to "TO HUMIDIFIER," pointing from the gases supply 130 end to the chamber 104 end. Similarly, the inspiratory conduit 122 can include arrows and optional text (e.g., "TO PATIENT") pointing from the chamber end to the user end, and the expiratory conduit 124 can include arrows and optional text (e.g., "FROM PATIENT") pointing from the user end to the gases supply end. Any suitable combinations or selection of shapes, colors, sizing, and/or symbols can be used to help a user make the desired connections and/or make the desired connections in the desired order. Further, in some embodiments, connectors of different components may be configured not to be able to connect to one another. For example but without limitation, the inspiratory conduit can have a connector that connects to only the outlet of the humidifier. In such embodiments, the connectors would reduce the likelihood of improperly connecting the component because the components would be very difficult, if not impossible, to connect incorrectly.

Figure 9A:
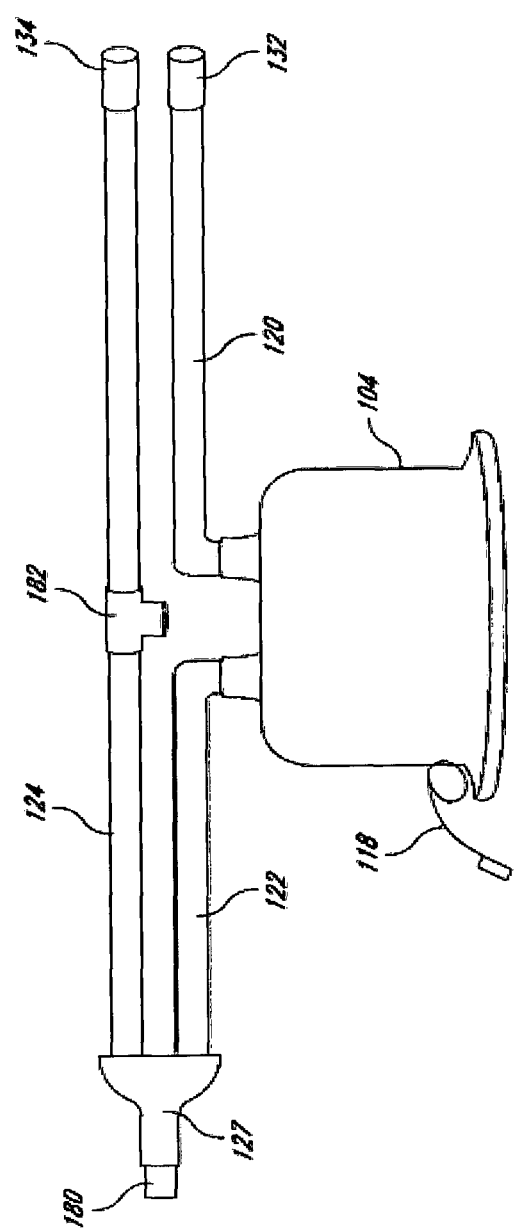
FIG. 9A illustrates an example embodiment of a one-piece circuit.

To further simplify set-up of the breathing circuit, in some embodiments, the supply 120, inspiratory 122, and, optionally, expiratory 124 conduits can be coupled into a one-piece circuit, for example as shown in FIG. 9A. In some embodiments, the user ends of the inspiratory 122 and expiratory 124 conduits can be coupled to a Y-piece 127 configured to be coupled to the interface 126 in use. The Y-piece 127 can be packaged with a disposable cap 180 covering the user end to help inhibit contamination of the conduits and connections during set-up. The electrical connectors and cables for temperature and flow sensors and heating elements can also be integrated into the one-piece circuit. In some embodiments, the chamber 104 can be provided pre-coupled with the one-piece circuit as well.

The conduits can be joined together or coupled via, for example, a mesh-type wrap or sheath surrounding at least some portion of the conduits. In some configurations, multiple portions of the conduits to be joined to form a multiple lumen structure can be joined with separate connecting means, including but not limited to mesh-type wrap, sheaths, belts, connectors, clips or the like. In some embodiments, the supply conduit 120 and inspiratory conduit 122 can be removably coupled to the expiratory conduit 124 with individual clips. This can advantageously allow for the expiratory conduit 124 to be unclipped from the supply 120 and inspiratory 122 conduits and removed from the circuit when not needed.

Figure 9B:
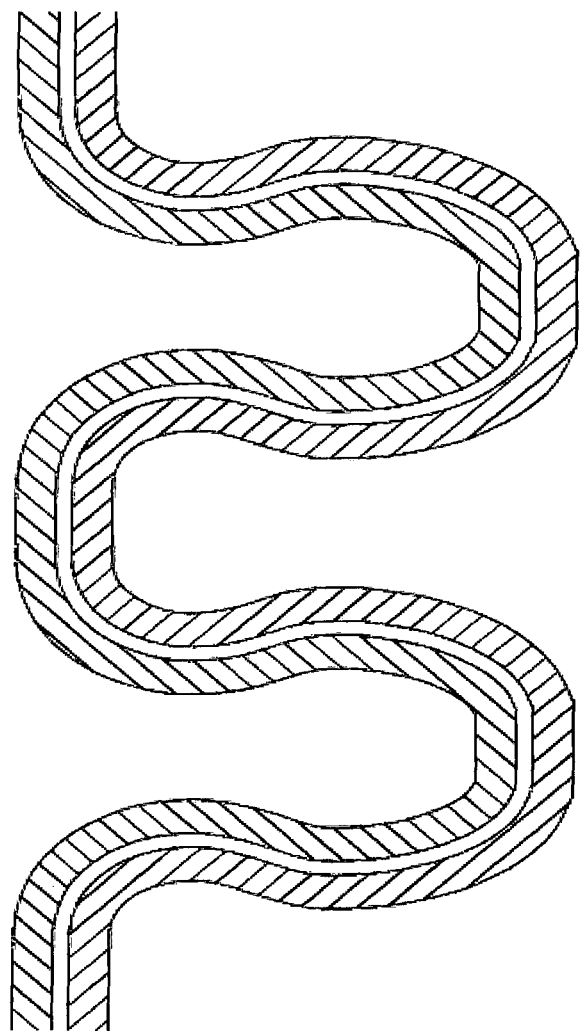
FIG. 9B illustrates an example embodiment of a releasable connection system for a one-piece circuit.

In some embodiments, two or more of the conduits are structured to releasably connect together. In some embodiments, all of the conduits are structured to releasably connect together. A first conduit (e.g., the inspiratory conduit) can comprise a first portion of one of a hook material or a loop material and a second conduit (e.g., the expiratory conduit) can comprise a second portion of the other of a hook material or a loop material. The first and second portions can be configured to releasably connect together in a hook-and-loop arrangement. Other releasable connection systems can additionally or alternatively be used, such as a series of magnets whereby the two portions include magnets of opposite polarity, for example but without limitation. In another configuration, the outer wall of the inspiratory conduit and the outer wall of the expiratory conduit can be corrugated such that the peaks and troughs of the corrugation are mushroom-shaped. In such a configuration, the peaks of one conduit are configured to releasably snap-fit into the troughs of the other conduit such as shown in FIG. 9B, for example but without limitation. In such a configuration, the conduits may be directly connected to one another. The size and shape of the peaks and troughs can be the same on both conduits or can be complementary to reduce or eliminate the likelihood of, for example but without limitation, two expiratory conduits connecting together.

The one-piece circuit advantageously reduces the number of connections required during set-up and reduces the possibility of incorrect assembly. Additionally, during set-up of traditional systems, the various components may be placed on a table or bed to allow for sorting and identification. Components can be misplaced or fall to the floor, thereby risking damage and/or contamination. The one-piece circuit advantageously helps reduce these problems. The one-piece circuit with integrated electrical connectors and cables also allows for the various electrical connections to be made during set-up with the components to be connected being positioned in close proximity to each other. In some embodiments, the expiratory conduit heating element connector plug 182 can be located along the length of the expiratory conduit 124 rather than at the gases supply 130 connector. The plug 182 can be positioned and configured to be connected to a socket on the sensor cartridge module 200 or elsewhere on the heater base 102, for example, on the front of the heater base 102 to improve visibility of and access to the socket. In such embodiments, the plug 182 may be automatically connected to sensor cartridge module 200 when the expiratory conduit 124 and/or the chamber 104 is connected to the heater base 102.

Various features can help improve the ergonomics of the humidification system 100. For example, the socket on the expiratory conduit gases supply end connector can be oriented at, for example, about a 45° angle from a plane defined by the end of the conduit. The angle can enhance the visibility of the socket when the expiratory conduit 124 is connected to either horizontally or vertically oriented gases supply 130 ports. The angle can also help reduce the likelihood that the socket will be obstructed by other components or equipment making set-up more difficult. The heater base 102 socket can be located on a front face of the heater base 102 to enhance visibility and ease of access as compared to placement of the socket on, for example, a side of the heater base 102 or elsewhere.

In some embodiments, the expiratory conduit 124 gases supply 130 end connector and/or the supply conduit 120 gases supply 130 end connector can have an elbow shape. For example, the connectors can have an angle of about 120°. The elbow shape can advantageously allow the operator to position the direction of the expiratory 124 and/or supply 120 conduits to and from the gases supply 130 so that the conduits do not obstruct other system components, such as the heater base 102 display. Any or all of the connectors, such as one or more of the expiratory conduit 124 and supply conduit 120 gases supply 130 end connectors and the inspiratory conduit 122 and expiratory conduit 124 user end connectors can include grip details to help the operator more easily grip the connectors and perform a twisting motion for inserting and removing medical taper connectors. The grip details can be especially beneficial for operators wearing surgical gloves.

In some embodiments, the heater base display 103 can be located on an upper surface of the spine 210, for example as shown in FIG. 11, for easier viewing. In the illustrated embodiment, the upper surface of the spine 210 and therefore the display 103 are oriented at an angle. The angled orientation can advantageously allow for an improved or easier view of the display 103 for the operator, particularly, for example, if the heater base 102 is positioned below the operator's horizontal line of sight. In some embodiments, the upper surface and/or display 103 can be oriented at an angle of about 22° from vertical, although other angles are also possible. In some embodiments, one or both of the supply conduit and inspiratory conduit chamber end connectors can have an angled or elbow shape. For example, in the embodiment of FIG. 11, the supply conduit chamber end connector 257 has an elbow shape so that it can be angled away from the heater base 102. The angled or elbow configuration can advantageously inhibit or prevent the connector and/or conduit from substantially obscuring the display 103, which serves to improve display visibility. In some embodiments, one or both of the supply and inspiratory conduit chamber end connectors can have an angle of about 112° so that the connector extends from the chamber port at an angle of about 22° above horizontal when coupled to the port, although other angles are also possible. In some embodiments, the spine 210, display 103, and/or one or both chamber end connectors can be configured so that the connector(s) is below the display 103 and/or a bottom edge of the upper surface of the spine 210, e.g., the connector(s) extends below a line extending from the bottom edge of the display 103 perpendicular to the plane of the display and/or below a line extending from the bottom edge of the upper surface of the spine 210 perpendicular to the plane of the upper surface.

Figure 10:
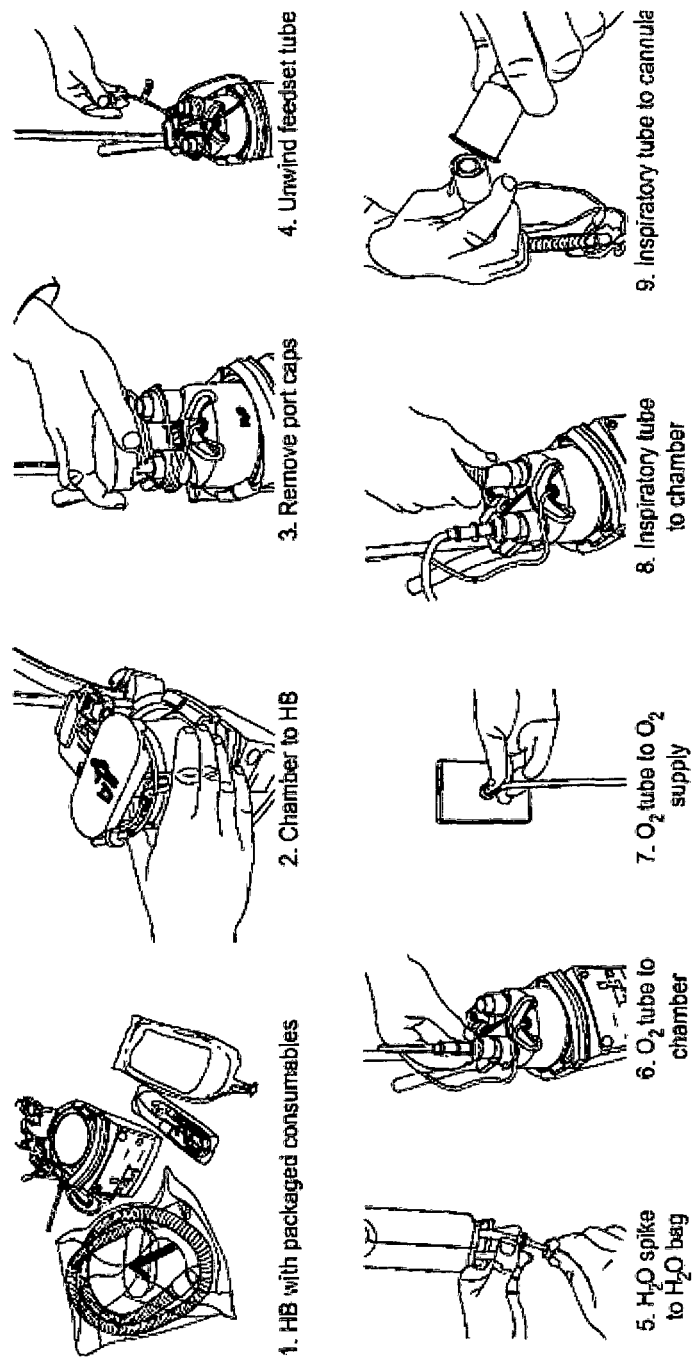
FIG. 10 illustrates a method for setting up a humidification system.

Additional features can assist the operator with the overall set-up process. For example, packaging for the consumable components of the system 100 can include a schematic diagram illustrating the set-up procedure and/or step-by-step instructions. FIG. 10 illustrates a sequential method for setting up a humidification system 100. The method can include some or all of: installing the chamber 104 on the heater base 102, removing the port cap(s) 160, 170, removing the spike 164 from the winder 166, unwinding the liquid conduit 118 and removing the winder 166 from the chamber 104, coupling the spike 164 to a liquid source, coupling the supply conduit 120 to the chamber inlet 110, coupling the supply conduit 120 to the gases supply 130, coupling the inspiratory conduit 122 to the chamber outlet 112, and coupling the inspiratory conduit 122 to the Y-piece 127 or interface 126. The method can further include coupling the expiratory conduit 124 to the interface 126 or Y-piece 127 and gases supply 130.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. While the description above refers to a "user," it should be noted that the ultimate user can be a patient and the apparatus described herein can be assembled by a nurse, doctor or other healthcare practitioner in a clinical or healthcare related facility as well as a user/patient in a home use, for example but without limitation. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Furthermore, dimensions of various components provided herein are exemplary, and other dimensions may be used. Thus, it is intended that the scope of the disclosure herein should not be limited by the particular embodiments described above.

What is claimed is:

1. A humidification apparatus comprising:
a humidification chamber configured to hold a volume of liquid and comprising:
at least one side wall;
a top wall connected to the at least one side wall;
a base surface connected to the at least one side wall;
a cavity being at least partially defined by the at least one side wall and the top wall;

an inlet port extending from the top wall, the inlet port surrounding and defining a passage into the cavity of the humidification chamber through the top wall;

an outlet port extending from the top wall, the outlet port surrounding and defining a passage out of the cavity of the humidification chamber through the top wall; and interlock features in the top wall, the interlock features being configured to mate with corresponding interlock features on a heater base to guide insertion of the chamber on the heater base, wherein the heater base comprises a sensor cartridge module comprising the interlock features of the heater base and at least one sensor probe separate from the interlock features, the interlock features of the chamber are configured to mate with the interlock features on the sensor cartridge module to guide connection of the chamber with the sensor cartridge module, the interlock features of the chamber comprise a male projection, and the interlock features of the heater base comprise a recess in the sensor cartridge module.

2. The humidification apparatus of claim 1, wherein the interlock features of the chamber and the corresponding interlock features of the heater base guide insertion of the chamber onto the heater base in a desired rotational orientation.

3. The humidification apparatus of claim 1, wherein the inlet port comprises a first sensor aperture, the first sensor aperture being configured to receive a first sensor mounted on the heater base, the outlet port comprising a second sensor aperture, the second sensor aperture being configured to receive a second sensor mounted on the heater base.

4. The humidification apparatus of claim 3, further comprising grommets positioned in the first and second sensor apertures, wherein the grommets pneumatically seal the first and second sensor apertures, the grommets being sized and shaped to receive the first and second sensors, and the grommets being configured to protect the first and second sensors from direct contact with gases passing into and out of the chamber such that the first and second sensors can be reused without cleaning.

5. The humidification apparatus of claim 1, wherein at least one of the at least one side wall and the top wall of the humidification chamber comprise features that define a front of the humidification chamber and a back of the humidification chamber, and wherein the chamber has a shorter vertical height on the back of the chamber and a taller vertical height on the front of the chamber to inhibit the chamber from being installed onto the heater base backwards.

6. A humidification apparatus comprising:

a heater base comprising a heater plate and a sensor cartridge module, the sensor cartridge module comprising at least one sensor and interlock features, the interlock features comprising a recess; and a humidification chamber configured to hold a volume of liquid, the heater plate configured to support the humidification chamber, and the humidification chamber comprising:

at least one side wall;

a top wall connected to the at least one side wall;

a cavity being at least partially defined by the at least one side wall and the top wall;

an inlet port extending through the top wall, the inlet port surrounding and defining a passage into the cavity;

an outlet port extending through the top wall, the outlet port surrounding and defining a passage out of the cavity; and interlock features in the top wall configured to mate with the interlock features on the heater base to guide insertion of the chamber onto the heater base, the interlock features comprising a male projection.

7. The humidification apparatus of claim 6, wherein the interlock features of the chamber and the interlock features of the base are configured to visually and physically guide insertion of the chamber onto the heater base in a desired rotational orientation.

8. The humidification apparatus of claim 6, the at least one sensor comprising first and second sensors, the first and second sensors being positioned vertically higher than the heater plate, the inlet port having a first sensor aperture configured to receive the first sensor, and the outlet port having a second sensor aperture configured to receive the second sensor.

9. The humidification apparatus of claim 8, wherein the interlock features of the chamber and the interlock features on the heater base are configured to mate to guide insertion of the chamber onto the heater base so that the first and second sensors are received in the first and second sensor apertures of the inlet and outlet ports at a desired depth.

10. The humidification apparatus of claim 8, further comprising grommets positioned in the first and second sensor apertures of the inlet port and outlet port, wherein the grommets pneumatically seal the first and second sensor apertures and are sized and shaped to receive the first and second sensors, and wherein the grommets are configured to protect the first and second sensors from direct contact with gases passing into and out of the chamber such that the first and second sensors can be reused without cleaning.

11. The humidification apparatus of claim 6, wherein at least one of the at least one side wall and the top wall of the chamber comprise features that define a front of the humidification chamber and a back of the chamber and are configured to guide insertion of the chamber onto the heater base with the back of the chamber towards the heater base.

12. The humidification apparatus of claim 11, wherein the chamber has a shorter vertical height on a back of the chamber and a taller vertical height on a front of the chamber to inhibit the chamber from being inserted onto the heater base backwards.

* * * * *